United States Patent [19]

Mowery, Jr.

[11] 4,095,472
[45] Jun. 20, 1978

[54] LIQUID SAMPLE DILUTION SYSTEM

[75] Inventor: Richard A. Mowery, Jr., Bartlesville, Okla.

[73] Assignee: Phillips Petroleum Company, Bartlesville, Okla.

[21] Appl. No.: 824,582

[22] Filed: Aug. 15, 1977

[51] Int. Cl.² .............................................. G01N 1/20
[52] U.S. Cl. ............................. 73/422 GC; 73/61.1 C
[58] Field of Search ........ 23/259; 73/422 GC, 422 R, 73/61.1 C

[56] References Cited

U.S. PATENT DOCUMENTS

| 3,701,716 | 10/1972 | Deuringer et al. | 23/259 |
| 3,934,456 | 1/1976 | Munk | 73/61.1 C |
| 4,036,062 | 7/1977 | Cruzan | 73/422 GC |

Primary Examiner—S. Clement Swisher

[57] ABSTRACT

A system is disclosed which enables one to intermittently obtain diluted samples of a liquid stream that reflect the composition of that liquid stream.

12 Claims, 1 Drawing Figure

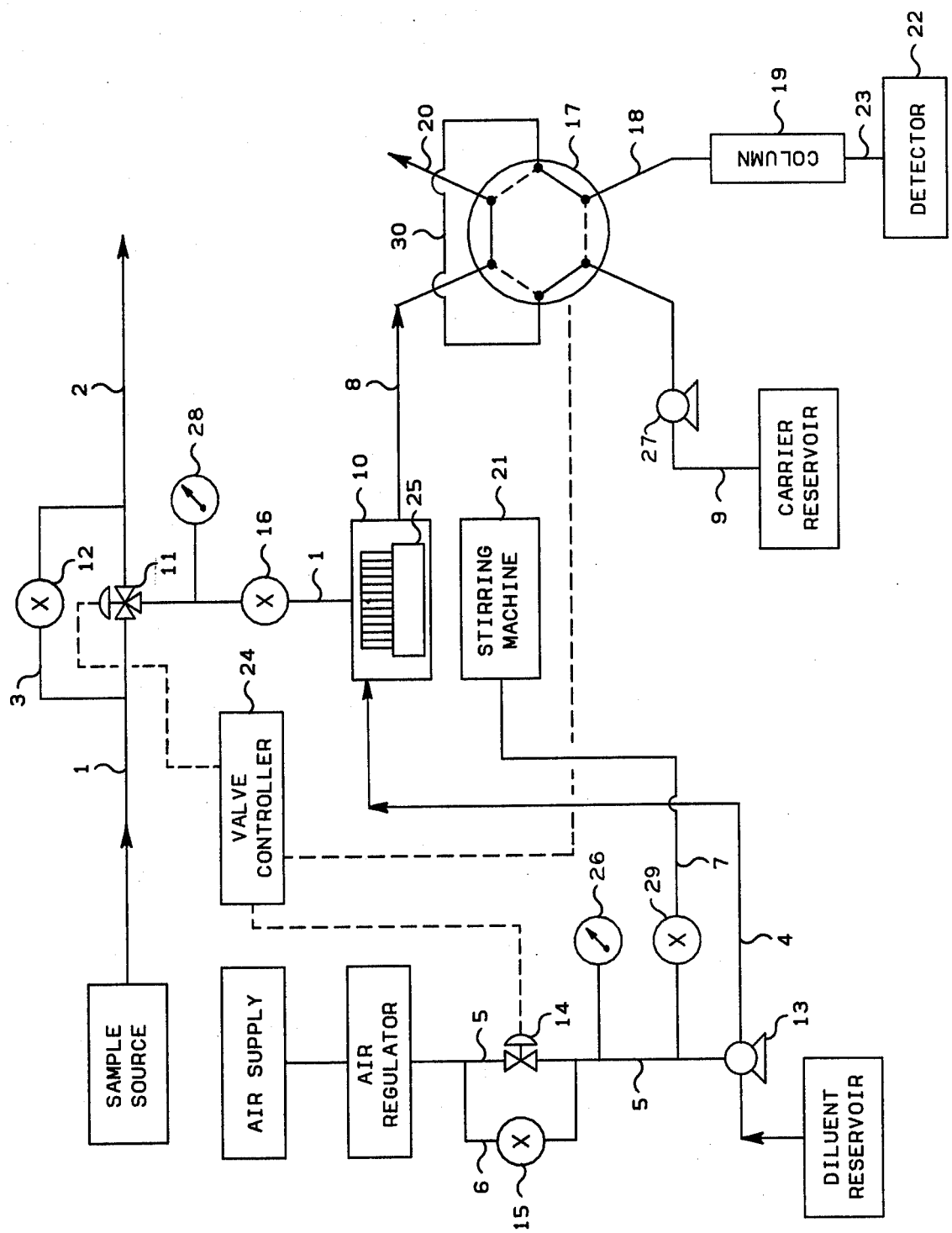

LIQUID SAMPLE DILUTION SYSTEM

This invention relates to an apparatus and method for diluting a sample material using a liquid diluent. In yet another aspect, the invention relates to an apparatus and method for automatic dilution of a sample material. In still another aspect the invention relates to dilution of a liquid sample for chromatographic analysis.

In the automatic sampling and analysis of fluids such as process fluids of a manufacturing plant, refinery, commercial chemical production system, or other similar process, it is often necessary to dilute the sample of process fluid prior to subjecting the sample to analysis or otherwise using the sample for a particular desired purpose. This is particularly true when the sample is so concentrated that a controlled dilution is necessary in order to bring the sample concentration to a level which is compatible with the use to which it will be put, or when the sample is too viscous to flow through a chromatographic column, even at high pressures. Other similar problems with high viscosity of the process fluid sampled and other similar physical and/or chemical characteristics of the sampled fluid make dilution, particularly a controlled dilution in which the dilution ratio remains constant and reproducible over a long period of time during which successive samples are diluted, desirable in conjunction with many processes or production systems. In many types of sampling apparatus, the smallest possible sample which can be taken is limited by physical restraints such as, for example, the minimum length of conduit used to connect the inlet and outlet ports of a sample loop in a sample valve. With the increasing sensitivity and accuracy of modern equipment such as chromatographic equipment, for example, it is often desirable to have even smaller samples of material to be analyzed since analysis of such smaller samples is well within the capability of the analyzing equipment, and use of smaller samples of material to be analyzed helps to shorten the time required for each analysis. By shortening the time required for each analysis cycle, an increased number of analysis cycles can be performed in a given time period thereby increasing the amount of work which can be done with a specified number of analyzers and/or increasing the resolution of process changes which may be reflected in the analysis of process fluids.

Accordingly, an object of the invention is to provide an apparatus and method for preparation of a fluid sample. Another object of the invention is to provide a method and apparatus for dilution of a fluid sample. Yet another object of the invention is to provide a method and apparatus for dilution of a fluid sample for chromatographic analysis. Still another object of the invention is to provide a method and apparatus for dilution of a liquid sample for liquid chromatographic analysis. Another object of the invention is to provide a fluid sample dilution system which allows purging between samples to be accomplished with a minimum amount of diluting liquid. Such a system is useful when the material being analyzed must be diluted with an expensive diluent.

Other aspects, objects, and advantages of the present invention will become apparent from a study of the disclosure, the appended claims, and the drawing.

The dilution apparatus of the present invention comprises (1) a mixing chamber wherein a stream of liquid diluent and a stream of sample liquid can combine to produce an effluent stream having a substantially constant concentration of the sample liquid, (2) an outlet from the mixing chamber, (3) a first conduit means providing a path of flow of sample liquid from a sample source into said mixing chamber, (4) a three-way valve in said first conduit between said sample source and said mixing chamber, (5) a second conduit means providing a path for flow from the second outlet of the three-way valve to a suitable discharge point, (6) a third conduit means providing a path for flow of sample liquid around said three-way valve from a point in the first conduit means upstream of said three-way valve to a point in the second conduit means, (7) a first restrictor in said third conduit means, (8) a second restrictor in said first conduit means between said three-way valve and said mixing chamber, and (9) a flow rate control means for controlling the rate of flow of liquid diluent into the mixing chamber.

A better understanding of the present invention will follow from a consideration of the drawing which is a schematic representation of a liquid chromatographic system employing a dilution apparatus within the scope of the present invention.

In the drawing a first conduit means 1 connects a sample source to a mixing chamber 10. The first conduit means contains a three-way valve 11. A second conduit means 2 is connected to the second outlet of three-way valve 11. A third conduit means 3 provides a path for flow of liquid around the three-way valve 11 from a point in conduit means 1 upstream of valve 11 to a point in conduit means 2. Conduit means 3 contains a restrictor 12. Conduit means 1 contains a restrictor 16 between the three-way valve 11 and the mixing chamber 10. A pressure gauge 28 is included in conduit 1 to reflect the rate of flow of sample liquid into the mixing chamber 10. A fourth conduit means 4 connects a diluent reservoir to the mixing chamber 10. In conduit means 4 is located an air actuated variable flow rate pump 13. A fifth conduit means 5 connects said pump 13 to a constant pressure source of air. In the drawing the constant pressure source of air is illustrated as an air supply connected to an air regulator which is in turn connected to conduit means 5. Conduit means 5 contains a valve 14. A sixth conduit means 6 is connected to conduit means 5 so as to provide a by-pass pathway around valve 14. The conduit means 6 contains a restrictor 15. A seventh conduit means 7 provides a path for air flow from a point in conduit means 5 downstream of restrictor 15 to an air actuated stirring machine 21. The seventh conduit means 7 contains a restrictor 29 which determines the flow rate of air to the stirring machine 21. A pressure gauge 26 is included in conduit 5 to monitor the air pressure on pump 13 and thus reflect the rate of flow of diluent. The outlet of the mixing chamber 10 is connected to a sample valve 17 by means of a conduit means 8. A conduit means 9 provides a path for flow of carrier liquid from a carrier reservoir to the sample valve 17. A pump 27 is provided in conduit means 9 for supplying carrier liquid from said carrier reservoir to sample valve 17. A conduit 18 connects the sample valve to a chromatographic column 19. A conduit 20 connects the sample valve to a discharge or recycle point. The chromatography column 19 is connected to a detector 22 by means of conduit 23. The apparatus also includes a valve controller 24 for controlling the positions of three-way valve 11, valve 14, and sample valve 17. Inside the mixing chamber 10 is located a magnetic stirring device 25 having a plurality of vertical blades which rotate about a vertical axis.

Preferably valves 11 and 14, as well as sample valve 17, are air actuated. Such valves could be electrically actuated but generally for safety considerations, it is desirable to have the flow system isolated from electrical connections. Restrictors 12, 15, 16 and 29 can consist of any suitable known means, including length as small diameter tubing, i.e. capillary tubing. Preferably one or more of the restrictors can be adjusted to provide different pressure drops.

The sample valve 17 can consist of any sample valve capable of trapping a specific volume of sample liquid and then allowing that volume to be driven through the column 19 by carrier liquid. In the drawing the sample valve schematically illustrated is a six-port, two-position valve. Detailed discussion of such sample valves can be found in U.S. Pat. Nos. 3,140,615 and 3,492,873, the disclosures of which are incorporated herein by reference. Air-actuated, six-port, two-position valves of this type can be obtained from Applied Automation, Inc., located in Bartlesville, Ok. In the drawing within the circle symbolizing the sample valve, the solid lines indicate the flow paths in the valve in one of its positions and the dotted lines indicates the flow paths in the valve in its other position.

It is to be noted that one could employ a sample valve of the type described in U.S. Pat. No. 2,846,121, the disclosure of which is incorporated herein by reference.

The column 19 can be any suitable chromatographic column capable of suitably selectively retarding the flow of the various components of the liquid samples that are to be tested.

The detector 22 can be any suitable means which will reflect the compositions of a liquid directed thereto.

The valve controller 24 can be any means suitable for controlling the switching of valves 11, 14 and 17. Preferably the valve controller is operated in response to a program, i.e. a time cycle. Any number of conventional programmers generally used in chromatographic analysis would be suitable for providing a program operated valve controller. A discussion of two such programmers can be found in U.S. Pat. Nos. 3,119,995 and 3,732,466, the disclosures of which are incorporated herein by reference.

The mixing chamber 10 as illustrated includes a magnetically operated stirring device 25, such as a commercially available fintail magnetic stirring bar, for example a fintail stirring bar of the type sold under the registered trademark of Spinfin. It is to be noted that it is within the scope of the present invention to employ any mixing chamber wherein a stream of liquid diluent and a stream of sample liquid can combine to produce an effluent stream having substantially constant concentration of said sample liquid. Accordingly, a stirring means in the mixing chamber is not absolutely essential. In a preferred embodiment, however, the mixing chamber contains a stirring device comprising a plurality of vertical blades which rotate about a vertical axis, the conduit 1 is connected to the mixing chamber such that sample liquid enters the mixing chamber by flowing downward onto the stirring device 25, the conduit 4 is connected to the sidewall of the mixing chamber such that liquid diluent entering the mixing chamber contacts the side surfaces of the stirring device 25, and the conduit 8 is connected to the sidewall of the mixing chamber at a point at least about 180° from the point at which conduit 4 is connected to the sidewall relative to the direction of rotation of said stirring device.

The apparatus illustrated can be operated as follows:

Conduit 5 receives air at a substantially constant pressure. When no liquid sample is being flowed into mixing chamber 10, valve 14 is positioned so that air for driving pump 13 must pass through conduit 6. The restrictor in conduit 6 causes the rate of flow of air to the pump 13 to be less than if valve 14 were positioned so that air could flow to the pump 13 directly through line 5. This results in the pump 13 delivering diluent liquid to the mixing zone at a slower rate than if valve 14 were positioned so that air could flow to the pump directly through line 5. It also results in the stirring device 25 turning slower than if valve 14 were positioned so that air could flow directly through line 5.

Conduit 1 is connected to a sample source providing liquid sample at a substantially constant pressure, for example from a process stream. Initially valve 11 is positioned so that no liquid sample can flow into the mixing chamber 10. Instead, the liquid passes to conduit 2 where it can be recycled back to the process stream or directed to some suitable point for disposal.

Intermittently, as desired, the valve controller 24 will position valve 11 so that no sample liquid can pass to conduit 2 through valve 11, but instead will pass through valve 11 into mixing chamber 10. The restrictors 12 and 16 control the rate at which the sample liquid flows into the mixing chamber when valve 11 is so positioned.

When valve 11 is positioned so that liquid sample is flowed into the mixing chamber, the valve controller 24 will position valve 14 so that air can travel through conduit 5 to speed up the rate at which diluent liquid is pumped into the mixing chamber and to speed up the rate at which the stirring device 25 turns.

Once a steady state is reached in which the effluent leaving the mixing chamber 10 via conduit 8 has a substantially constant concentration of sample liquid, the valve controller can actuate the sampling valve 17 first to trap a sample of the diluted sample liquid and then to cause that trapped sample to be forced through the column 19 by carrier liquid supplied by conduit 9. It should be noted that the diluent liquid and the carrier liquid are sometimes the same, in which case they can be supplied from a common source.

In trapping a sample of the diluted sample liquid, the sample valve 17 is switched to provide therein flow paths illustrated by the dotted lines. Thus the liquid in line 8 passes into the sample valve through the sample loop 30 of a known volume, and then to conduit 20 for disposal or recycling. When the column is switched back to the position providing flow paths therein illustrated by solid lines, the carrier liquid supplied via conduit 9 passes into the sample valve 17, through the sample loop 30 and finally to the column 19 via conduit 18. In this manner, the diluted liquid sample trapped in the sample loop is forced through the column 19 for separation so that its composition can be analyzed by the detector 22.

After a sufficient amount of diluted liquid sample has exited the mixing chamber for trapping in sample valve 17, the valve controller 24 returns valves 11 and 14 to their first described positions. Thus the flow of liquid sample to the mixing chamber is cut off, the flow rate of liquid diluent to the mixing chamber decreased, and the rate of turning of the stirring device is lowered. The rate of flow of liquid diluent into the mixing chamber 10, is this the low flow rate stage, is that which is sufficient to substantially cleanse the mixing chamber 10 of sample liquid prior to the next introduction of sample liquid to the mixing chamber. Thus this invention enables one to continually obtain diluted samples for analysis while minimizing unnecessary waste of diluent liquids.

It is to be understood that the specific embodiment of the present invention shown in the drawing and described above has been provided for the purpose of illustration of the broad invention. Further variations and modifications of the structure, materials, and uses disclosed may be made without departing from the scope of the claimed invention.

What is claimed is:

1. An apparatus for intermittently providing diluted samples from a sample source, said apparatus comprising,
   (1) a mixing chamber wherein a stream of liquid diluent and a stream of sample liquid can combine to produce an effluent stream having a substantially constant concentration of said sample liquid,
   (2) an outlet from said mixing chamber,
   (3) a first conduit means providing a path for flow of sample liquid from a sample source into said mixing chamber,
   (4) a three-way valve in said first conduit between said sample source and said mixing chamber,
   (5) a second conduit means providing a path for flow from the second outlet of said three-way valve to a suitable discharge point,
   (6) a third conduit means providing a path for flow of sample liquid around said three-way valve from a point in the first conduit means upstream of said three-way valve to a point in the second conduit means,
   (7) a first restrictor in said third conduit means,
   (8) a second restrictor in said first conduit means between said three-way valve and said mixing chamber, and
   (9) a fourth conduit means providing a path for flow of liquid diluent from a liquid diluent source into said mixing chamber, and
   (10) a flow rate control means for controlling the rate of flow of liquid diluent into the mixing chamber 2. An apparatus according to claim 1 wherein said flow rate control means for controlling the rate of liquid diluent into the mixing chamber comprises a variable flow rate pump positioned for transmitting said liquid diluent from said source of liquid diluent to said mixing chamber.

3. An apparatus according to claim 2 wherein said variable flow rate pump is actuated by air supplied through a fifth conduit means, said fifth conduit means contains a valve means between said pump and the source of air for cutting off the flow of air through said fifth conduit, a sixth conduit providing a path for air flow from a point in said fifth conduit means upstream of said valve means in fifth conduit means to a point in said fifth conduit means downstream of said valve means in said fifth conduit means, and a third restrictor in said sixth conduit means.

4. An apparatus according to claim 3 wherein said first conduit means is connected to a first inlet of said mixing chamber, said third conduit means is connected to a second inlet of said mixing chamber, said mixing chamber contains a stirring device comprising a plurality of vertical blades which rotate about a vertical axis, said first inlet being positioned in the top of said mixing chamber so that sample liquid enters said mixing chamber by flowing downward onto said stirring device, said second inlet being positioned in the sidewall of said mixing chamber, and said outlet of said mixing being positioned in the sidewall of the mixing chamber at least about 180° from the second inlet relative to the direction of rotation of said stirring device.

5. An apparatus according to claim 4 wherein said stirring device is a magnetic fintail stirring bar and a stirring machine associated with said mixing chamber in such fashion as to cause said stirring bar to rotate inside said mixing chamber.

6. An apparatus according to claim 5 wherein said magnetic stirring machine is actuated by air supplied through a seventh conduit means which provides for air flow from a point in said fifth conduit means downstream of said third restrictor.

7. An apparatus according to claim 6 including means to measure the flow rate of liquid sample into the mixing chamber and means to measure the flow rate diluent into the mixing chamber.

8. An apparatus according to claim 7 including means for intermittently actuating said three-way valve to intermittently allow sample liquid to flow into said mixing chamber and means for actuating said valve means in fourth conduit means intermittently to reduce the flow rate of air to said variable flow rate delivery pump when no sample liquid is flowing into said mixing chamber.

9. A liquid chromatographic analysis apparatus comprising a column for effecting the separation of components of a liquid sample; a detector means for detecting the components of a liquid sample as they are eluted from said column; an apparatus according to claim 8; a sample valve connected to the outlet of said mixing chamber to a source of carrier liquid and to said column, said sample valve being capable of trapping a specific volume of liquid flowing from said mixing chamber and then allowing that volume to be driven through said column by said carrier liquid; and means for actuating said sample valve means to effect the trapping of diluted samples and the driving of those samples through the column.

10. A liquid chromatographic analysis apparatus comprising a column for effecting the separation of components of a liquid sample; a detector means for detecting the components of a liquid sample as they are eluted from said column; an apparatus according to claim 1; a sample valve connected to the outlet of said mixing chamber to a source of carrier liquid and to said column, said sample valve being capable of trapping a specific volume of liquid flowing from said mixing chamber and then allowing that volume to be driven through said column by said carrier liquid; and means for actuating said sample valve means to effect the trapping of diluted samples and the driving of those samples through the column.

11. A method for intermittently effecting chromatographic analysis of a sample liquid comprising
   passing a flow of sample liquid into a mixing chamber at a constant flow rate while a flow of liquid diluent is also passed into said mixing chamber at a first constant flow rate to produce a diluted effluent stream which has a substantially constant concentration of said sample liquid,
   trapping a specific volume of said diluted effluent stream,
   stopping the flow of said sample liquid into said mixing chamber after a sufficient amount of diluted effluent stream for trapping has exited said mixing chamber, then reducing the flow rate of liquid diluent to any rate which is sufficient to substantially cleanse the mixing chamber of sample liquid prior to the next introduction of a flow of sample liquid to the mixing chamber, and effecting chromatographic separation of the trapped volume of said diluted effluent stream.

12. A method for intermittently effecting chromatographic analysis of a sample liquid stream employing an apparatus according to claim 9 comprising;

directing said sample liquid stream at a constant pressure into said first conduit means with said three-way valve in a first position in which no sample liquid can flow to said mixing chamber;

connecting said variable flow rate pump to a source of diluent liquid;

directing air at a constant pressure into the fourth conduit means with the valve in said fourth conduit means positioned in a first position in which the air, in order to reach the variable flow rate pump, must pass through the fifth conduit means;

intermittently positioning the three-way valve in said first conduit means in a second position such that no sample liquid pass to said second conduit through said three-way valve, but instead sample liquid flow to the mixing chamber;

positioning the valve means in the fourth conduit means in a second position so that air can travel freely through said fourth conduit means to speed up the rate at which diluent liquid is pumped into the mixing chamber as sample liquid is passed into the mixing zone, effecting mixing of said liquid sample stream and said diluent liquid stream in said mixing chamber to produce a diluted effluent stream having substantially constant concentration of sample liquid which exits said outlet of said mixing chamber, actuating said sample valve first to trap a sample of said diluted effluent stream for analysis and then to allow the trapped sample to be driven through the chromatographic column by carrier liquid, detecting at least one characteristic of the material eluting from the column, returning said three-way valve means to said first position when the amount of diluted effluent stream which has exited said mixing chamber is sufficient for trapping in said sample valve, returning said valve means in said fourth conduit to said first position so that the flow rate of diluent to the mixing chamber is reduced when liquid sample is no longer flowing into said mixing chamber.

* * * * *

UNITED STATES PATENT AND TRADEMARK OFFICE
CERTIFICATE OF CORRECTION

PATENT NO. : 4,095,472
DATED : June 20, 1978
INVENTOR(S) : Richard A. Mowery, Jr.

It is certified that error appears in the above-identified patent and that said Letters Patent are hereby corrected as shown below:

Column 6, line 18, after "rate" and before "diluent" insert therefor --- of liquid ---.

Signed and Sealed this

Sixteenth Day of January 1979

[SEAL]

Attest:

RUTH C. MASON
Attesting Officer

DONALD W. BANNER
Commissioner of Patents and Trademarks